United States Patent [19]

Anisovich et al.

[11] 4,091,282
[45] May 23, 1978

[54] X-RAY FLUORESCENCE SPECTROMETER

[76] Inventors: Kliment Vladislavovich Anisovich, prospekt Maxima Gorkogo 67, kv. 16; Nikolai Ivanovich Komyak, Kostromskoi prospekt, 22, kv. 71, both of, Leningrad, U.S.S.R.

[21] Appl. No.: 724,231

[22] Filed: Sep. 17, 1976

[30] Foreign Application Priority Data

Sep. 26, 1975 U.S.S.R. .............................. 2174672

[51] Int. Cl.$^2$ ............................................. G21K 1/06
[52] U.S. Cl. .................................. 250/280; 250/272; 250/277 CH
[58] Field of Search ................ 250/272, 273, 277 CH, 250/280

[56] References Cited
U.S. PATENT DOCUMENTS

| | | | |
|---|---|---|---|
| 2,805,341 | 9/1957 | Lang ..................................... | 250/280 |
| 2,805,343 | 9/1957 | Lang ..................................... | 250/280 |
| 3,514,599 | 5/1970 | Campbell ............................. | 250/272 |

*Primary Examiner*—Archie R. Borchelt
*Attorney, Agent, or Firm*—Lackenbach, Lilling & Siegel

[57] ABSTRACT

Disclosure is made of an X-ray fluorescence spectrometer comprising an X-ray source, a holder of a sample being investigated, an analyzing crystal which focuses the fluorescent radiation of the sample installed in the holder, and a detector which records the radiation reflected from the analyzing crystal. The distance between the X-ray source and the sample holder is such as to ensure an illumination of the central portion of the sample's surface not less than $15Z$ erg/s·cm$^2$·W, wherein $Z$ defines the atomic weight of the X-ray anode, at a voltge of 50 kV across the X-ray source. The sample holder is so arranged with respect to the focal circle that the distance between the latter and the sample's surface exposed to radiation is not in excess of the product of the distance between the source's focus and the sample's surface exposed to radiation by the ratio between the diameter of the focal circle and the length of the analyzing crystal.

3 Claims, 2 Drawing Figures

X-RAY FLUORESCENCE SPECTROMETER

The present invention generally relates to spectrometers and, more particularly to X-ray fluorescence spectrometers intended for quantitative chemical analysis in ferrous and non-ferrous metallurgy, geology, chemical industry, etc.

There are known Soller spectrometers which are X-ray fluorescence spectrometers with plane parallel plates. The sensitivity of these spectrometers is determined by the primary radiation (erg/sec) directed at a sample being investigated, i.e. by the X-ray tube's power. The sensitivity of such spectrometers can only be improved by raising the power of the X-ray tube, which involves designing and manufacturing problems.

A decrease in the distance between the tube's focus and the sample's surface exposed to radiation cannot raise the sensitivity because the primary radiation, upon which the sensitivity is dependent, is always constant.

There are also known Johann and Johansson spectrometers. In these focusing, diffraction-by-a-crystal, X-ray fluorescence spectrometers use is made of a curved crystal. The sensitivity of such a spectrometer is determined by the illumination of a sample's portion being investigated by the primary radiation of an X-ray tube (erg/sec·cm$^2$). The sample's area exposed to radiation is quite large, which is due to a great distance between the sample's surface and the focal circle; hence, a high-power X-ray tube is required to provide for a desired degree of illumination of the sample's working portion. Thus, the sensitivity of the spectrometer is raised through raising the power of the X-ray tube, which involves the above-mentioned difficulties. A reduction in the distance between the tube's focus and the surface of the sample being investigated does not bring about a desired improvement of the sensitivity, because the degree of illumination is increased only in the sample's central portion, but is reduced over the sample's periphery, whereby, on the whole, the illumination is practically the same.

There are still further known X-ray fluorescence spectrometers of a type that comprises an X-ray source, a sample holder arranged on the radiation path of the source, an analysing crystal which focuses the fluorescent radiation of a sample installed in the holder and defines a focal circle by the curve of its planes, and a detector which records the radiation reflected from the analysing crystal.

In such a spectrometer, the sample's surface is inside the focal circle, which accounts for a small area of the sample's working portion. However, the sensitivity of such spectrometers is limited because the X-ray source is far from the surface of the sample being investigated, wherefore the illumination of this surface is poor.

The sensitivity of such spectrometers can be improved by increasing the power of the X-ray tube; however, this is undesirable for reasons that are stated above.

It is the main object of the present invention to substantially improve the aperture ratio of the X-ray fluorescence spectrometer.

It is another object of the invention to raise the spectrometer's sensitivity without increasing the power consumption.

It is still another object of the invention to provide a highly sensitive, small-size X-ray fluorescence spectrometer.

The foregoing and other objects of the present invention are attained by providing an X-ray fluorescence spectrometer comprising an X-ray source, a sample holder arranged on the radiation path of the X-ray source, an analysing crystal which focuses the fluorescent radiation of a sample installed in the holder and defines a focal circle by the curve of its planes, and a detector which records the radiation reflected from the analysing crystal, in which spectrometer the X-ray source is spaced, in accordance with the invention, from the sample holder at a distance which ensures an illumination of the central portion of the sample's surface at not less than $15Z$ erg/s·cm$^2$·W, wherein Z is an atomic weight of material of the X-ray anode at a voltage of 50 kV across the X-ray source, whereas the sample holder is so located with respect to the focal circle that the distance between the latter and the sample's surface exposed to radiation is not in excess of the product of the distance between the source's focus and the sample's surface exposed to radiation by the ratio between the diameter of the focal circle and the length of the analysing crystal.

One may select the distance between the focus of the source and the sample's surface exposed to radiation to be not greater than one quarter of the height of the analysing crystal; the distance between the sample's surface exposed to radiation and the focal circle may be selected to be not greater than one quarter of the product of the focal circle's diameter by the ratio between the height and length of the analysing crystal.

The optimum results are attained if the location of the X-ray source relative to that of the sample holder is selected so as to ensure a minimum distance between the focus of the source and the sample's surfaces exposed to radiation.

The X-ray fluorescence spectrometer of the present invention makes it possible to raise the sensitivity 10 to 30 times through increasing the aperture ratio, without any increase in the power of the X-ray tube; it is also possible to reduce the power of the X-ray tube two to three orders, without loss of sensitivity. The use of a low-power X-ray tube of the type with a small distance between the focal spot and outlet aperture makes it possible to substantially reduce the size and production cost of the spectrometer.

Other objects and advantages of the present invention will become more apparent from the following detailed description of preferred embodiments thereof to be read in conjunction with the accompanying drawings, wherein.

Figure 1:
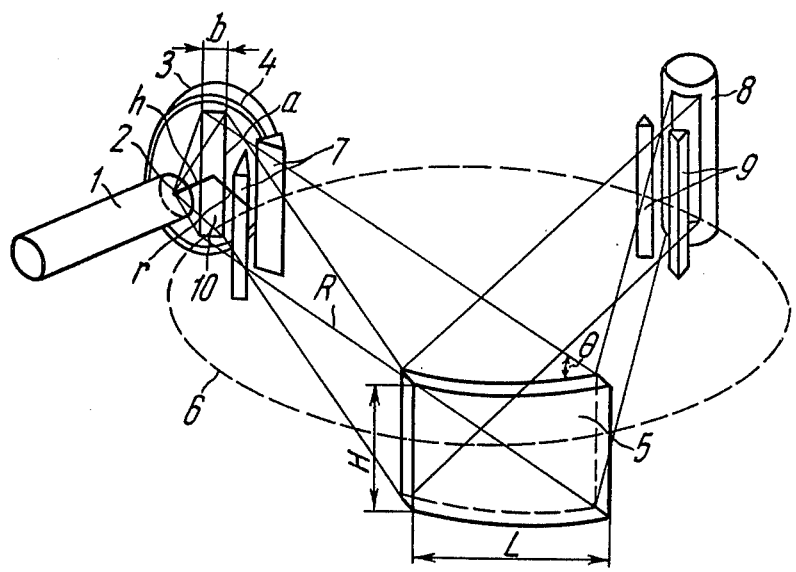
FIG. 1 is an isometric view of the optical circuit of an X-ray fluorescence spectrometer in accordance with the invention.

Referring now to the attached drawings, the proposed X-ray fluorescence spectrometer of FIG. 1 comprises an X-ray source which is an X-ray tube 1 with a focal spot 2, and a sample holder 3 arranged across the radiation path of the tube 1. In FIG. 1, the proposed spectrometer is shown with a sample 4 which is a pellet placed in the holder 3. The spectrometer further includes a focusing analysing crystal 5; the curve of the latter's planes determines the location of a focal circle 6. The crystal 5 has a height H and a length L. On the focal circle 6, opposite the sample holder 3, there is arranged an entrance slit 7; opposite a detector 8, which records radiation reflected by the analysing crystal 5, there is arranged an output slit 9. The function of the detector 9 may be performed, for example, by a proportional gaseous discharge counter. On the surface of the sample 4, which is exposed to radiation, there must be investigated a zone 10 having a height "a" and a width "b."

The height "a" of the zone 10 to be investigated is limited by the height of the analysing crystal 5 and is equal to H. The width "b" of the zone 10 is determined by the distance "r" between the surface of the zone 10 and the focal circle 6.

$$b = rL\sin\theta/R = rL/D,$$

where
R is the distance between the entrance slit 7 and the analysing crystal 5;
$D = R/\sin\theta$ is the diameter of the focal circle 6;
$\theta$ is the Bragg angle.

The distance "h" between the focal spot 2 of the tube 1 and the surface of the sample 4 exposed to radiation is determined by the position of the X-ray tube 1 relative to the sample holder 3; this position is selected so as to ensure an illumination of the central portion of the sample 4 of not less than $15 Z$ erg/s·cm²·W, wherein Z defines an atomic weight of material of the X-ray anode, at a voltage of 50 kV across the tube 1.

The distance "r" is selected to be not in excess of this value: $r = h D/L$.

Keeping in mind that most of the existing focusing analysing crystals have a height of 1 to 4 cm, "h" can be selected to be not greater than one quarter of the height H of the analysing crystal 5. In this case the sample holder 3 is arranged so that the distance "r" between the surface of the sample 4 exposed to radiation and the focal circle 6 should not be in excess of this value: DH/4L.

The illumination of the central portion of the sample 4 is the best when the distance "h" between the focal spot 2 of the tube 1 and the surface of the sample 4 exposed to radiation is selected to be as small as possible.

Figure 2:
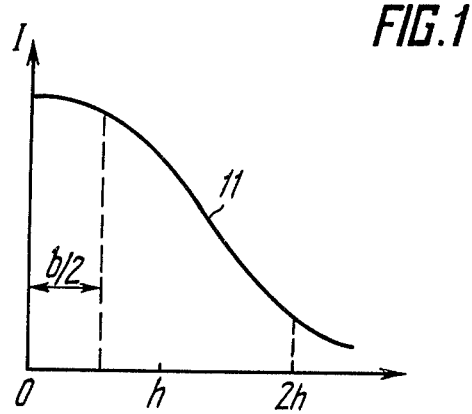
FIG. 2 is a curve showing the relationship between the intensity of fluorescence of illuminated portions of a sample and their spacing from the center of the illuminated zone.

In FIG. 2, a curve 11 shows the relationship between the fluorescence intensity of the illuminated portions of a sample and the distance therefrom to the center of the illuminated area. Plotted on the abscissa is the distance between a portion of the sample and the latter's center; plotted on the y-axis is the intensity of fluorescence measured in erg/sec·cm².

The X-ray fluorescence spectrometer of the present invention operates as follows.

The primary radiation of the X-ray tube 1 (FIG. 1) coming from the focal spot 2 illuminates the sample 4, wherein the secondary X-ray fluorescent radiation is induced. The fluorescent radiation of the sample 4 passes through the entrance slit 7, is reflected from the analysing crystal 5, focused on the output slit 9 and recorded by the detector 8.

The sensitivity of the proposed spectrometer is determined by the illumination of the zone 10 of the sample 4, which is being investigated. A reduction in the area of the zone 10 causes a corresponding reduction in the radiation of the tube 1 and, hence, an increase in the aperture ratio.

If the condition $r \leq h D/L$ is complied with, and if "h" is selected to ensure an illumination of the sample's surface of not less than $15Z$ erg/s·cm²·W, where Z defines an atomic weight of material of the anode, at a voltage of 50 kV across the source, $b = rh/D \leq h$. In this case, the illumination of the zone 10 of the sample 4 is uniform throughout its width (a); as regards the lengthwise distribution of illumination, the level of $15Z$ erg/s·cm²·W, wherein Z defines an atomic weight of material of the X-ray anode, is observed only in the central portion of the zone 10 and decreases towards the periphery. Although illumination is kept within the specified limits only in the central portion of the zone 10, the mean illumination of the zone 10, which determines the spectrometer's aperture ratio, is quite great because of the small area ("a" × "b") of the zone 10 of the sample 4, which accounts for a high sensitivity of the spectrometer and low power consumption.

Similarly, if the requirement $r \leq DH/4L$ (with "h" not being in excess of H/4) is complied with, the width "b" of the zone 10 of the sample 4 is not greater than $H/4 = h$. In this case, the illumination is uniform throughout the width of the zone 10 of the sample 4. Lengthwise, the maximum illumination is observed only in the central portion of the zone 10 and decreases towards the periphery. The extreme vertical points of the zone 10 are spaced from the center by the value of $a/2 = H/2 = 2h$; such a distance between the focal spot 2 and the surface of the sample 4 makes it possible to expose the portion of the surface being investigated practically to the whole of the radiation flux of the X-ray tube 1 in the vertical plane (see FIG. 2). In this case, the illumination is also sufficiently great, while the area being investigated is small, which accounts for a high aperture ratio of the spectrometer.

The best results are obtained when "h" is kept at a minimum and the condition $r \leq h D/L$ is complied with, because in this case the minimum possible area of the zone 10 is combined with the maximum possible mean illumination, which accounts for a high sensitivity of the spectrometer.

In the embodiment under review, the sample's portion to be investigated is quite small. Therefore, in order to average out the results of the analysis, the sample should be shifted in the course of measurements.

According to this disclosure, the function of the dispersing element is performed by an analysing crystal. Of course, this does not imply that the latter cannot be replaced by a technical equivalent, for example, a focusing diffraction grating.

FIG. 1 shows an embodiment of the present invention with the sample holder 3 arranged outside the focal circle 6. It is possible to place the sample holder inside the focal circle, but the embodiment of FIG. 1 yields the optimum results.

An X-ray fluorescence spectrometer has been built according to FIG. 1. This spectrometer employs an acute-focus five-watt X-ray tube; "h" is selected to be equal to 5 mm; r is 3 mm; and D is 300 mm. The spectrometer also makes use of a lithium fluoride Johansson analysing crystal with H = 20 mm, and L = 60 mm, the detector being a xenon proportional counter. The illumination of a sample's central portion is $1.2 \cdot 10^4$ erg/sec·cm²·wt.

While recording pure cobalt fluorescence, the pulse rate is 150.000 pulses per second, which corresponds to 30.000 pulses/sec.wt. and is two orders higher than the pulse rates of conventional spectrometers.

With a five-watt tube, the sensitivity of the spectrometer amounts to $n \cdot 10^{-4}\%$, which corresponds to the sensitivity of conventional spectrometers with tube powers of more than 1 kV. The spectrometer is marked by a small size (about 300×300×200 mm) and small weight (about 30 kg).

What is claimed is:

1. An X-ray fluorescence spectrometer comprising an X-ray source; a sample holder arranged across the radiation path of said X-ray source, said sample holder being spaced from said X-ray source at a distance which ensures an illumination of the central portion of said sample's surface not less than $15Z$ erg/s·cm$^2$·w, wherein Z defines an atomic weight of the X-ray anode, at a voltage of 50 kV across said source; an analyzing crystal which focuses the fluorescent radiation of said sample placed in said sample holder; the curve of the planes of said analyzing crystal defining a focal circle, said sample holder being so arranged with respect to said focal circle that the distance between the latter and the surface exposed to radiation of said sample placed in said sample holder is not in excess of the product of the distance between the focus of said source and said surface exposed to radiation of said sample by the ratio between the diameter of said focal circle and the length of said analyzing crystal; and a detector which records radiation reflected from said analyzing crystal.

2. An X-ray fluorescence spectrometer as claimed in claim 1, wherein said distance between the focus of the source and the surface of the sample exposed to radiation is not in excess of one-fourth of the height of said analysing crystal, whereas said distance between the surface of the sample exposed to radiation and the focal circle is not in excess of one-fourth of the product of the diameter of said focal circle by the ratio between the height and length of said analysing crystal.

3. An X-ray fluorescence spectrometer as claimed in claim 1, wherein said X-ray source is positioned with respect to said sample holder so as to ensure a minimum distance between the focus of the source and the surface of the sample exposed to radiation.

* * * * *